United States Patent [19]

Ueda et al.

[11] Patent Number: 5,033,475
[45] Date of Patent: Jul. 23, 1991

[54] PORTABLE ELECTROCARDIOGRAPHIC RECORDING ANALYZER FOR MONITORING DISCONTINUOUS TIME PERIODS OF WAVEFORMS

[75] Inventors: Morikazu Ueda, Tokyo; Sadatsugu Takahashi, Ebina; Youitsu Ohara, Yokohama, all of Japan

[73] Assignee: Medical Instrument Japan Co., Ltd., Yokohama, Japan

[21] Appl. No.: 457,793
[22] PCT Filed: Jun. 1, 1989
[86] PCT No.: PCT/JP89/00554
§ 371 Date: Jan. 8, 1990
§ 102(e) Date: Jan. 8, 1990
[87] PCT Pub. No.: WO89/11821
PCT Pub. Date: Dec. 14, 1989

[30] Foreign Application Priority Data

Jun. 2, 1988 [JP] Japan .................... 63-136553

[51] Int. Cl.$^5$ .................... A61B 5/0452
[52] U.S. Cl. .................... 128/704
[58] Field of Search .............. 128/696, 702, 704, 705, 128/710

[56] References Cited

U.S. PATENT DOCUMENTS

| | | | |
|---|---|---|---|
| 3,606,882 | 9/1971 | Abe et al. | 128/704 |
| 3,799,148 | 3/1974 | Rowen | 128/704 |
| 3,824,990 | 7/1974 | Baule | 128/702 |
| 3,952,731 | 4/1976 | Worstencroft | 128/702 |

Primary Examiner—William E. Kamm
Attorney, Agent, or Firm—Armstrong, Nikaido, Marmelstein, Kubovcik & Murray

[57] ABSTRACT

A portable electrocardiographic recording analyzer incorporates means for counting the total sum of P, Q, R, S, T and U waves of electrocardiographic waveforms larger than a set reference voltage for a certain period of time; means for storing the preceding counted values; means for setting a reference value for the difference between the two means; signal means operating to issue an output when the difference between the value counted by the counting means and the value stored by the storing means is larger than a predetermined value; recording means for recording electrocardiographic waveforms in discontinuous periods of time which are set as desired; and means for storing an electrocardiographic waveform obtained when the signal means issues the output, along with an electrocardiographic wavform obtained at the preceding step. This analyzer can be used for monitoring in the domain of mental and nervous diseases, for monitoring of patients suffering from various diseases under hospital or home treatment, for use as a life monitoring apparatus for a serious case, as well as for monitoring of patients under medical treatment for cardiac or cerebral diseases.

3 Claims, 2 Drawing Sheets

PORTABLE ELECTROCARDIOGRAPHIC RECORDING ANALYZER FOR MONITORING DISCONTINUOUS TIME PERIODS OF WAVEFORMS

TECHNICAL FIELD

This invention relates to a small, light, portable electrocardiographic recording analyzer which enables cardiac functions to be observed electrophysiologycally by means of an electrocardiogram, which alarms the user when an abnormality is detected, and which can be always carried by a patient having a potential abnormality in the cardiac or cerebral functions in order to detect the abnormality at an early stage.

BACKGROUND ART

As is well known, the percentage of tragic results caused by various troubles dangerous to life (e.g., heart stroke and cerebral hemorrhage) can be reduced if the occurrence of the relating abnormality is immediately detected to enable administration of first aid.

However, no means has been provided which enables a device for detecting this kind of abnormality to be put to widely practical use in complete systems. Ordinarily, electrocardiograms are used for the prediction of abnormalities or for searching for evidence of such.

In electrocardiogram tests, however, unlike abnormal waves always present such as those relating to organic degeneracy diseases (typically, arrhythmia and so on), abnormal waves temporarily generated (e.g., of myocardial infarction) cannot be detected unless they are accidentally generated during electrocardiogram recording.

For the purpose of compensating for this drawback, a portable electrocardiogram recorder is carried for a long time to detect in a magnetic tape record a fit wave which may be generated at an unpredictable time. This system is known as Halter electrocardiograph.

In the Halter electrocardiograph, however, a magnetic tape used for recording is played back afterward by a special reproduction analyzer in a medical institution to reproduce waveforms, and the existence and the number of abnormal waves and the forms of the waves are not made clear until the reproduction. The halter electrocardiograph is therefore useless in immediately taking measures to meet the situation at the time of the emergence of abnormal waves.

DISCLOSURE OF THE INVENTION

The inventor of the present invention has eagerly studied in consideration of the above-described problems of the conventional art to achieve the present invention.

The present invention provides a portable electrocardiographic recording analyzer, comprising: means for counting the sum total of the P, Q, R, S, T and U waves of electrocardiographic waveforms larger than a set reference voltages for a certain period of time; means for storing the preceding counted values: means for setting a reference value for the difference between the two sets of voltages signal means operating to issue an output when the difference between the value counted by said counting means and the value stored by said storing means is larger than a predetermined value: recording means for recording electrocardiographic waveforms for discontinuous periods of time which are set as desired; and means for storing an electrocardiographic waveform obtained when the signal means issues the output, along with an electrocardiographic waveform obtained at the preceding step.

The present invention has been achieved on the basis of the apparatus for measuring abnormal electrocardiographic signals disclosed in Japanese Patent Publication No. 56-22538 and includes an improvement on the same. That is, the measuring apparatus described in Japanese Patent Publication No. 56-22538 relates to an apparatus for measuring abnormal electrocardiographic signals for diagnosing the state of the subject in such a manner that the total sum of the number of waves larger than a set reference voltage exhibited for a certain period of time and the total sum of the number of waves in the next certain period of time are compared with each other. An output is obtained when the difference between these total sums reaches a certain reference value and is used for the diagnosis. An abnormality detection signal is supplied to an alarm device to effect alarming.

The electrocardiographic recording analyzer of the present invention is made by improving this apparatus and is provided with the means for recording electrocardiographic waveforms for discontinuous periods of time which are set as desired, and for storing in the memory the electrocardiographic waveform obtained at a preceding stage when an alarm is issued by the signal means.

The electrocardiographic recording analyzer of the present invention records electrocardiographic waveforms such as those shown in FIG. 2. In FIG. 2, A represents a state in which the heart is normal, B represents a state in which an abnormal state proceeds, and C represents a state in which the abnormal state proceeds and virtually terminates.

In a case where an abnormality (such as a change in S or T, or arrhythmia) is sensed, a buzzer (alarm signal) for alarming the user for the occurrence of the abnormality is output, and data on whether or not any other abnormalities have been exhibited in the electrocardiograph is simultaneously stored in the memory retroactively relative to the occurrence of the abnormality.

When the subject is diagnosed in a medical institution, the stored data can be reproduced in an electrocardiograph of the medical institution which is of a type purchased in the market, thereby enabling a doctor to analyze the waveforms without selecting a special analyzer.

In this event, various brands of analyzers may be used by the medical institution to be directly connected to the electrocardiograph through the input terminal, thereby enabling display of the electrocardiogram.

In cases of emergency, the stored electrocardiogram may be transmitted to the medical institution by using a telephone line. It is thus easy to cope with any emergency situation.

If there are a plurality of operators in the hospital or medical institution who can simultaneously work in a sickroom, ICU, CCU and the like, concentrative monitoring can be effected with FM wireless controllers.

The electrocardiographic recording analyzer of the present invention can continuously generate an alarm sound to call someone for emergency treatment and lifesaving in cases where the person carrying the analyzer in a serious crisis and loses consciousness.

BEST MODE FOR CARRYING OUT THE INVENTION

The present invention will be described in more detail with respect to an embodiment thereof, but it will be obvious that the present invention is not limited to the embodiment.

Figure 1:
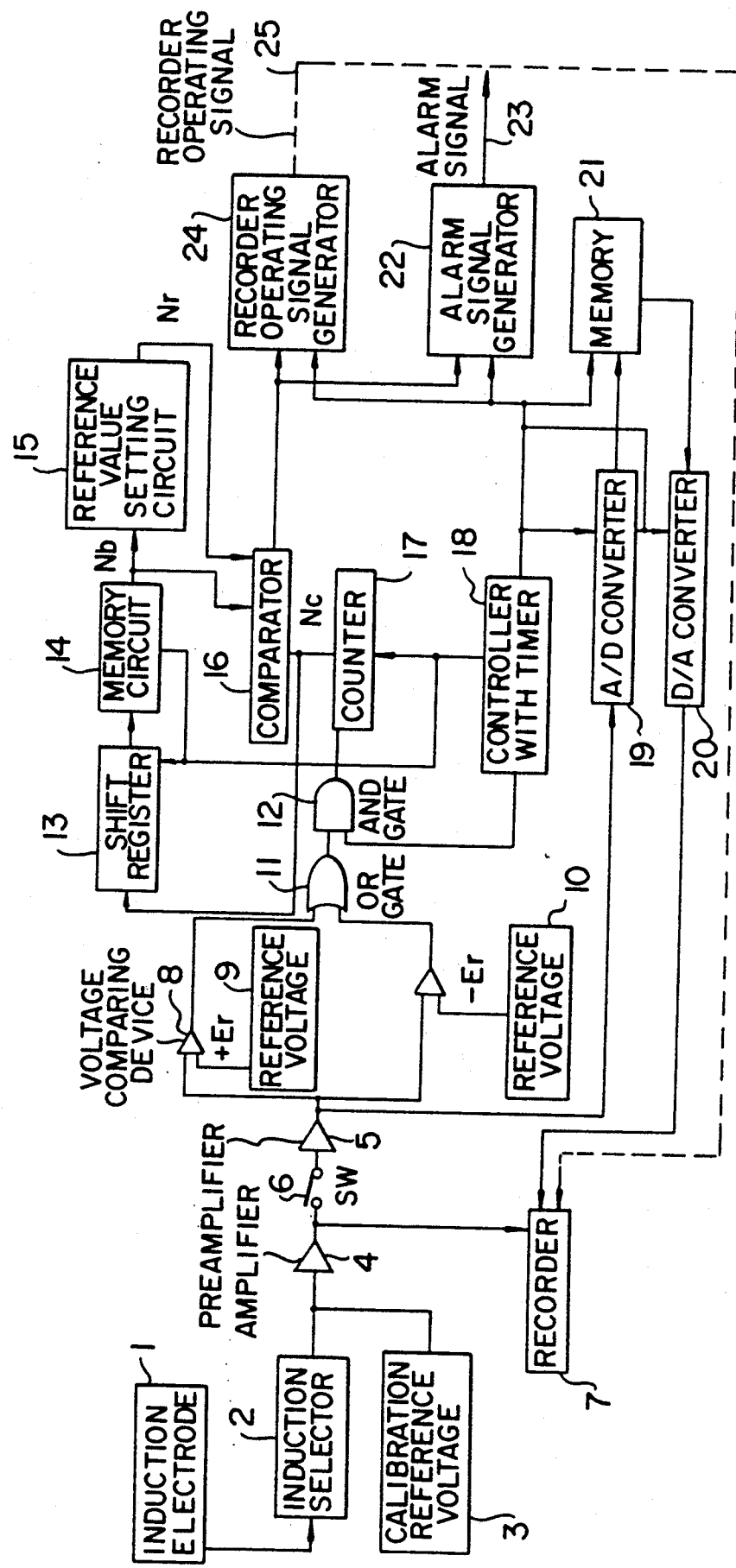
FIG. 1 is a block diagram of analyzer which represents an embodiment of the present invention.
Figure 2:
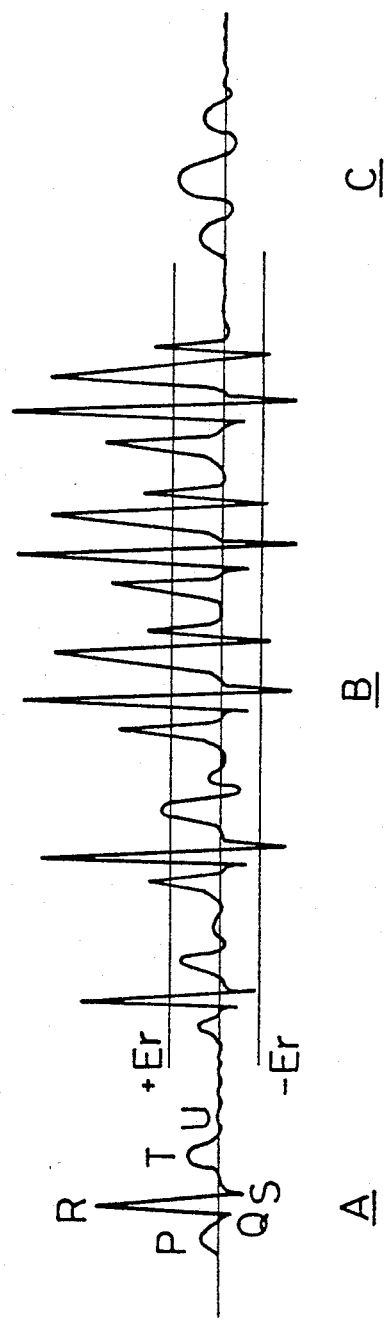
FIG. 2 is a diagram of electrocardiographic waveforms.

FIG. 1 is a diagram showing an embodiment of the present invention. While an electrocardiographic signal is supplied from an introduction electrode 1 attached to an arm or leg of a human body and is input into an electrocardiogram recorder 7 via an induction selector 2 (i.e., an amplifier 4) the signal is input into a preamplifier 5 of an electrocardiographic recording analyzer in accordance with the present invention via a switch 6. An output from the preamplifier 5 is connected positive and negative voltage comparing devices (analog comparators 8) to which a positive reference voltage 9 + Er and a negative reference voltage 10 − Er are connected. The preamplifier is also connected to a memory means 21 via an A/D converter 19 to always store and monitor the electrocardiographic signal (waveform). Outputs from the voltage comparing device 8 are in turn input into a counter 17 having counting means via an OR gate 11 and an AND gate 12.

A timer and a controller 18 are connected to the counter 17 and to the AND gate 12 to supply a count setting time signal and a clear signal. The input to the counter 17 is further supplied to a comparator output means serving as a comparator 16. In addition, an output from the counter 17 is stored in a memory circuit (memory means) 14 through a shift register 13. This memory circuit 14 is connected to the comparator 16 and a reference value setting circuit (reference value setting means) 15, and the reference value setting circuit 15 is connected to the comparator 16. A recorder operating signal generator 21 and an alarm signal generator 22 are connected to the comparator 16 and to the controller 18, and the memory means 21 is connected to the controller 18 through the A/D converter 19, thereby enabling the recorder operating signal 25 from the recorder operating signal generator 24 to be input into the electrocardiogram recorder 7. Electrocardiographic waveforms obtained during discontinuous periods of time which are set as desired are thereby recorded. At the time of occurrence of an abnormality, electrocardiographic waveforms obtained in certain periods of time before and after the corresponding point of time are stored in the memory 21, and these electrocardiographic waveforms are reproduced in the recorder 7 through a D/A converter 20 when necessary.

The counter 17 counts, in the electrocardiographic waveforms, the total number Nc of waves larger than the reference voltages ±Er and obtained during a certain time period, and supplies this number to the comparator 16.

The shift register 13 is supplied with the output from the counter 17 and stores in the memory circuit 14 the value obtained at the preceding time and to thereby supply the comparator 16 with the number of outputs Nb issued from the voltage comparing device 8 during the preceding certain period of time.

The reference value setting circuit 15 produces a preset reference value Nr and supplies the same to the comparator 16. The comparator 16 calculates the difference between the above-mentioned Nb and Nc and issues an output when this difference is larger than the reference value Nr.

The present invention is constructed as described above and therefore operates in such a manner that the number of waves of electrocardiographic waveforms larger than the set reference voltage and the output from the voltage comparing device 8 is input into the OR gate 12 and the AND gate. The number of waveforms obtained at the preceding time is input into the memory circuit 14 and the reference value setting circuit 15 thereby continuously comparing the total sum Nb of the number of waves input into the comparator 16 for a certain period of time (e.g., one minute) and the total sum Nc of the number of waves obtained in the next one minute. Those sum totals are input into the comparator 16 from the OR gate 11, AND gate 12 and the counter 17 When there is a change in a difference between the total sums Nb and Nc and when this difference reaches the certain reference value Nr set by the reference value setting circuit 15. the recorder operating signal generator 24, the alarm signal generator 22 and the memory 21 operate to record the electrocardiographic waveforms in a period of time set as desired and to store the electrocardiographic waveforms obtained in certain periods of time before, during and after the corresponding time point.

That is, the portable electrocardiographic recording analyzer of the present invention enables the subject to realize the occurrence of any abnormality in the electrocardiogram. The present invention records the kind of the abnormality which would warrant informing the subject of whether or not he or she must contact a doctor. Thus, the analyzer of the invention is very effective in protecting of the life of patients suffering from various kinds of diseases or of aged persons.

As described above, the portable electrocardiographic recording analyzer of the present invention records the electrocardiogram of the patient at set times for set periods of time. The analyzer memorizes and monitors the electrocardiogram, alarms the subject to make him or her realize the abnormality has been detected and stores the electrocardiogram in the memory retroactively as past data, thereby enabling the abnormality to be detected at an early stage and enabling the taking measures immediately.

The portable electrocardiographic recording analyzer of the present invention has improved effects described above, and can be used for various purposes. Among the potential applications for the present invention are the monitoring mental and nervous diseases, the monitoring patients suffering from various diseases under hospital or home treatment, the use as a life observation apparatus, the life care of medical facilities, for monitoring in physical strength measurements or load tests relating to sports, measurements in sports facilities, as well as the monitoring of patients under medical treatment for cardiac or cerebral diseases.

What is claimed is:

1. A portable electrocardiographic recording analyzer comprising:
    detection means for detecting and measuring first and second sets of P, Q, R, S, T and U waves of electrocardiographic waveforms, each set detected and measured over a predetermined period of time at consecutive first and second times, respectively;

voltage comparing means connected to said detection means for comparing the first and second sets of P, Q, R, S, T and U waves with predetermined voltage references;

first memory means connected to said detection means for storing electrocardiographic waveforms of the first and second sets of P, Q, R, S, T and U waves;

counting means connected to said voltage comparing means for counting a number of first and second P, Q, R, S, T and U waves that have exceeded the predetermined voltage references within the predetermined periods of time during the consecutive first and second times, respectively;

storing means connected to said counting means for storing a count of the first set of P, Q, R, S, T and U waves during the first time;

comparator means connected to said counting means and said storing means for comparing the number of first P, Q, R, S, T and U waves exceeding the predetermined voltage references with the number of second P, Q, R, S, T and U waves exceeding the predetermined voltage references, said comparator means also for calculating a difference between the compared numbers of waves, further said comparator means for generating an output signal that an abnormality in the calculated difference between the compared number of waves has occurred;

electrocardiographic recording means connected to said detection means, said first memory means and said comparator means for recording electrocardiographic waveforms of sets of P, Q, R, S, T and U waves after receiving the output signal from said comparator means;

alarm signal means connected to said comparator means for generating an alarm signal after receiving the output signal from said comparator means;

controller means connected to said first memory means, said electrocardiographic recording means and said alarm signal means for controlling operation of said first memory means, said electrocardiographic recording means and said alarm signal means;

reference value setting means connected to said comparator for setting a predetermined reference difference between the compared number of first and second sets of P, Q, R, S, T and U waves so as to provide a reference for the comparator means when to generate the output signal.

2. A portable electrocardiographic recording analyzer as set forth in claim 1, wherein
said electrocardiographic recording means records electrocardiographic waveforms of the first and second sets of P, Q, R, S, T and U waves and a third set of P, Q, R, S, T and U waves during a third time from said detection means and from said first memory means after receiving the output signal from said comparator means, the third time occurring after the output signal.

3. A portable electrocardiographic recording analyzer as set forth in claim 1 or 2, further comprising:
output D/A converter means connected to said electrocardiographic recording means for converting electrocardiographic waveforms stored in said electrocardiographic recording means into a recorder output signal for transmission to and reproduction in a recorder.

* * * * *